US00PP11956P2

(12) United States Plant Patent
Letlow

(10) Patent No.: US PP11,956 P2
(45) Date of Patent: Jun. 26, 2001

(54) *GELSEMIUM SEMPERVIRENS* CONROP

(75) Inventor: James Cloice Letlow, Theodore, AL (US)

(73) Assignee: Plant Development Services Inc., Loxley, AL (US)

( * ) Notice: Subject to any disclaimer, the term of this patent is extended or adjusted under 35 U.S.C. 154(b) by 0 days.

(21) Appl. No.: 09/346,897

(22) Filed: Jul. 2, 1999

(51) Int. Cl.[7] ..... A01H 5/00
(52) U.S. Cl. ..... Plt./226
(58) Field of Search ..... Plt./226

*Primary Examiner*—Bruce R. Campell
*Assistant Examiner*—Annette Para

(57) ABSTRACT

A new and distinct *Gelsemium sempervirens* plant which possesses a compact growth habit and fragrant yellow flowers.

1 Drawing Sheet

BACKGROUND OF THE INVENTION

This new Gelsemium variety named 'Conrop' was found as a sport of *Gelsemium sempervirens*, an unpatented variety, maintained by Flowerwood Nursery, Inc. in Mobile, Ala. The sport, hereinafter referred to as 'Conrop', was discovered by James Cloice Letlow in 1993. The value of this new cultivar lies in its unique compact growth habit. 'Conrop' has retained many of the outstanding attributes of the species, in particular its tolerance of insects and diseases which makes it adaptable to culture in the Sunbelt states. Asexual propagation of the new plant by cuttings has been under Mr. Letlow's direction at the same location. Several generations of the new plant have been evaluated and the distinctive characteristics of the plant have remained stable. The plant cannot be reproduced true from seed.

SUMMARY OF THE INVENTION

The following are the most outstanding and distinguishing characteristics of this new cultivar when grown under normal horticultural practices in Mobile Ala.

1. Low compact growth habit.
2. Flowers are single, fragrant, and Yellow Group 7A.
3. Easily propagated with semi-hardwood cuttings in late spring through the summer.
4. Fast growth rate under normal fertilization and moisture conditions.
5. Tolerates full sun to shade.
6. Good specimen plant.
7. Desirable in planters.
8. Good ground cover.
9. Attractive glossy evergreen foliage.
10. Hardy to Zone 6.

DESCRIPTION OF THE DRAWINGS

The new *Gelsemium sempervirens* variety is illustrated by the accompanying photographic prints in which.

1.

2.

Figure 1:
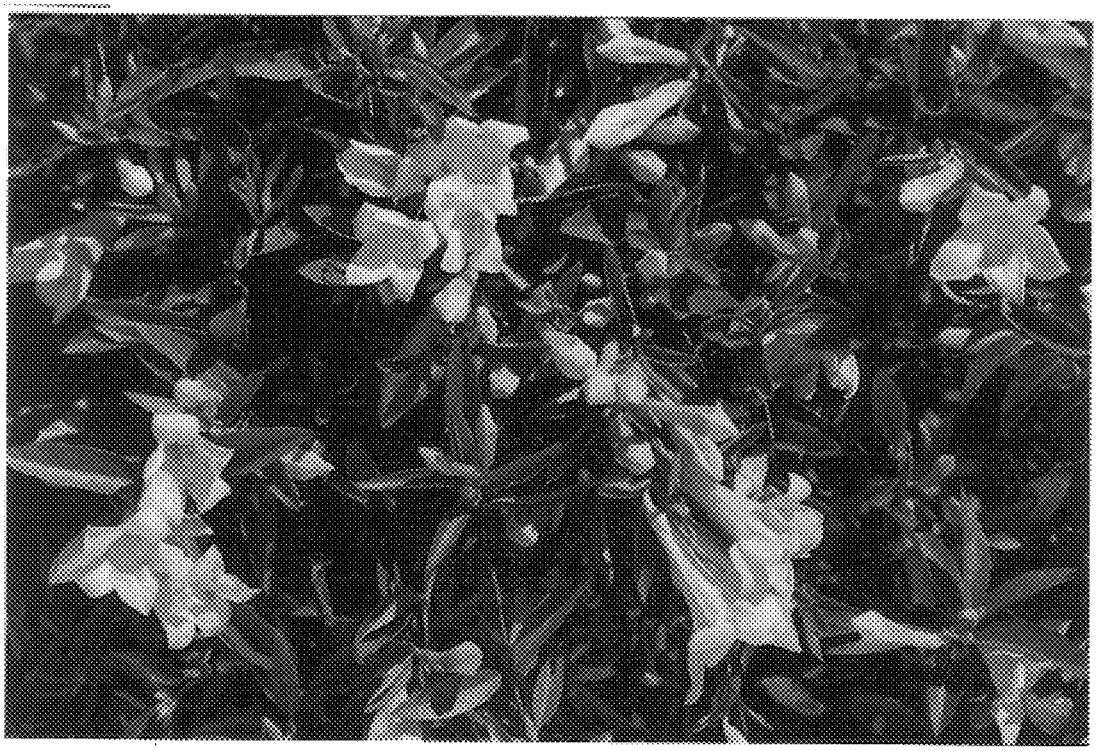
FIG. 1 is a close-up showing flower, foliage, and stem color as well as flower form.
Figure 2:
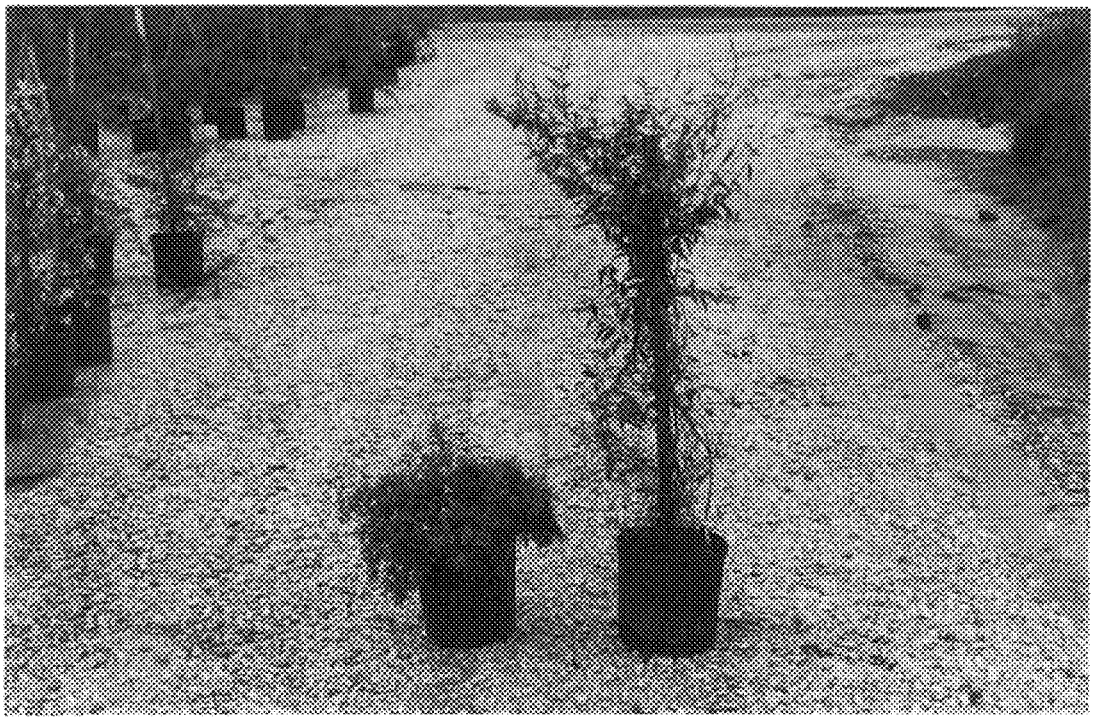
FIG. 2 is a side-by-side photograph of an un-named specimen of the species *Glesemium sempervirens* (on the right) and the new variety 'Conrop' (on the left). This photograph, which was taken in early spring, shows the low, compact growth habit of the new variety as compared to the twining habit of the parent.

The observed plant in FIG. 2 is a 28 month old plant grown in a three gallon container under normal growing conditions in Mobile, Ala. The growing medium is a 1 pine part pine bark and 3 part sand mix.

The colors shown are as true as is reasonably possible to obtain by conventional photographic procedures. The colors of the various plant parts are defined with reference to The Royal Horticultural Society Colour Chart. Description of colors in ordinary terms are present where appropriate for clarity in meaning.

BOTANICAL DESCRIPTION OF THE PLANT

The following is a detailed description of the new variety of Gelsemium based on my observations made of plants grown in wholesale commercial production practices, in greenhouses, and in established landscape plantings in Mobile, Ala.

Distinctive Characteristics:

| Characteristic | Gelsemium s. 'Conrop' | *Gelsemium sempervirens* (the species) | *Gelsemium rankinii* (the species) |
|---|---|---|---|
| Height (Mature) | 2–3' | 10–20' | 10–20' |
| Width (Mature) | 3–4' | 8–10' | 8–10' |
| Bloom Time | March 1 | March 1 | March 14 & Fall |
| Petal Number | 5 | 5 | 5–6 |
| Style Length | ¾–1" | ¾–1" | ¼–⅜" |
| Filament Length | ¼–7/16" | ¼–½" | ¾–1" |
| Stamen Number | 5 | 5 | 4–6 |
| Leaf Length | 1¼–1¾" | 1¾–2" | ⅞–2½" |
| Leaf Width | ⅜–⅝" | 7/16–⅝" | ⅝–1" |
| Flower Length | ⅞–1⅛" | 1–1⅜" | 1–1⅜" |
| Flower Width | ¾–1" | ⅞–1¼" | ⅞–1¼" |
| Fruit Size | ½–¾" | ½–¾" | ¼–½" |

'Conrop' originated from the plant Loganiaceae *Gelsemium sempervirens*. The genus named Gelsimium was proposed by Antoine Laurent de Jussieu (1748–1836). The species name *sempervirens* was first used by Carlos Linneaus (1707–1778) with another plant genus and was first used with Gelsemium by William Townsend Aiton (1766–1849).

The species *Gelsemium rankinii* is similar to the species *sempervirens*, however, its' bloom time and its' flower structures are different. The fruit is also smaller than that of the species *Gelsemium sempervirens*.

Classification:

*Botanic.*—*Gelsemium sempervirens* 'Conrop'.

*Height.*—2–3'.

*Width.*—3–4'.

*Growth habit.*—Low, compact and rounded.

*Growth rate.*—Medium to fast under normal fertilization and moisture conditions. Mature height is 2–3' and width 3–4'. This varies greatly from the parent species which is a vine which can grow to 20' tall. Rooted cuttings can be produced in three to four months when propagated in late spring in Mobile, Ala. In a period of four years from a rooted cutting the new variety 'Conrop' reaches a height of 20" and spread of 24". Under the normal growing conditions in Mobile, Ala. the growth rate is normally about 4 to 5" per year while maintaining a dense habit due to the abundant branch developement and short internode lengths.

*Foliage.*—Opposite, simple, evergreen, lanceolate, glabrous, 1¼" to 1¾" long and ⅜" to ⅝" wide. Apex is acute or acuminate, base rounded and margins are entire. The petioles are 1/16" to 3/16 long and leaf venation is pinnate. The petiole diameter is 1/32 to 1/16". The upper surface of the immature leaf is Yellow-Green 144A, glossy, and glabrous. The underside is Green Group 143C and matte. The upper surface of the mature leaf is Green Group 137A, glossy, and glabrous and the underside is Green Group 137D and matte. There are occasional alternate foliaceous stipules which are ⅛ to 3/16" long and 1/32 to 1/16" wide. The upper surface is Yellow-Green Group 144A and the underside is Yellow-Green Group 144B. The stipules are non-caducous. In 1997, the date of initial spring growth was Mar. 14, in Mobile, Ala. After the initial spring flush, there was almost continuous growth until fall, ending Oct. 25, also in Mobile, Ala. When grown in full sun, the internode length of this plant is ¼" to ⅝"; when grown in light shade, the internode length of this plant is ½" to 1⅛". As would be expected, a plant grown in the shade results in a taller, less dense plant with larger leaves.

*Stems.*—The young shoots are Yellow-Green Group 144B, slender, glabrous, and matte. In about six months they change to Greyed-Purple Group 183A and are often covered with a waxy grayish bloom. Stems mature to Greyed-Green Group 197A and after a year or so become rugose. The immature stem diameter is 1/16" and matures to ⅛". The plant is densely branched throughout the entire shrub. The pith is solid and uniform.

*Flowers.*—Perfect, single, fragrant, axillary, borne on pervious year's wood, ⅞–1⅛" long and ¾–1" wide, solitary or in clusters of 2–3, funnel form with 5 short lobes. The bloom is Yellow Group 7A front and back and the throat of the bloom is Yellow-Orange Group 14A. The pedicel is ⅛–¼" long, scaly, and Yellow-Green Group 144B. The calyx is also Yellow-Green Group 144B and the five lobes are lanceolate with acute tips. There is one pistil, slender styled, 2-cleft, each divided again and appearing 4-cleft. The style is Yellow-Green Group 145C and ¾ to 1" long. The five stamens are ¼ to 7/16 long with filaments Yellow Group 2C. The anthers are ⅛" long, Yellow Group 7A and the pollen is Yellow Group 7B. There is a four to six week flowering period normally beginning in early March in Mobile, Ala. There is sporadic flowering in the summer and fall. The blooms last on the plant in the garden three to five days. A mature plant may have several hundred flowers.

*Fruit.*—Compressed, ½to ¾" long and ⅜ to ½" wide, short-beaked, oblong capsule. Each capsule contains 8–12 membranously winged seeds which are ¼ to ⅜" long. The capsule matures from Yellow-Green Group 144A in the spring to Brown Group 200C in September and October. The capsule opens in late fall to release the seeds which are Greyed-Yellow Group 161A. Normal fruit set is not heavy.

*Culture.*—Grows well in a wide range of conditions and tolerates sun to shade. Perfers a moist, well-drained soil rich in organic matter but is adaptable; responds well to mulching and medium applications of fertilzer; perfers ph 5 to 6.5; best flowering in full sun but will grow and flower in shade; very little pruning is needed. Cold hardiness and drought resistance are comparable to the parent species. Propagated with semi-hardwood cuttings in late spring through the summer.

*Pests.*—None serious

I claim:

1. A new and unique variety of *Gelsemium sempervirens* plant named 'Conrop' as herein shown and described.

* * * * *